US00PP12552P2

(12) United States Plant Patent
Olesen et al.

(10) Patent No.: US PP12,552 P2
(45) Date of Patent: Apr. 16, 2002

(54) CLIMBING ROSE VARIETY 'POULNORM'

(76) Inventors: L. Pernille Olesen; Mogens N. Olesen, both of Hillerødvejen 49, DK-3480 Fredensborg (DK)

( * ) Notice: Subject to any disclaimer, the term of this patent is extended or adjusted under 35 U.S.C. 154(b) by 0 days.

(21) Appl. No.: 09/276,892

(22) Filed: Mar. 25, 1999

(51) Int. Cl.[7] ..... A01H 5/00
(52) U.S. Cl. ..... Plt./115
(58) Field of Search ..... Plt./115, 112, 109

(56) References Cited

PUBLICATIONS

UPOV–ROM GTITM Computer Database 2000/06, Dec. 6, 2000, GTI Jouve Retrieval Software, citation for 'Poulnorm'.*

* cited by examiner

*Primary Examiner*—Bruce R. Campell
*Assistant Examiner*—June Hwu

(57) ABSTRACT

A new garden rose plant which has abundant, large red, fragrant flowers and attractive foliage. This new and distinct variety has shown to be uniform and stable in the resulting generations from asexual propagation.

2 Drawing Sheets

SUMMARY OF THE INVENTION

The present invention constitutes a new and distinct variety of garden rose plant which originated from a controlled crossing between an unnamed seedling (non-patented) and 'Norita' (non-patented.) The two parents were crossed and the resulting seeds were planted in a controlled environment. The new variety is named 'POULnorm'.

The new rose may be distinguished from its seed parent, an unnamed seedling, by the following combination of characteristics:

1. The seed parent has pink blooms; whereas, 'POULnorm' has red blooms;
2. The habit of the seed parent is shrubby and compact; whereas, 'POULnorm' is a climber;
3. The petalage of the seed parent is semi-double, whereas 'POULnorm' has very double and much Larger blooms.

The new variety may be distinguished from its pollen parent, 'Norita', by the following combination of characteristics:

1. The blooms of the pollen parent are a darker red when compared to the blooms of 'POULnorm';
2. The pollen parent is a hybrid tea rose with a shruby habit; whereas, 'POUnorm' has the growth habit of a climber;
3. The petalage of the pollen parent is double compared to 'POULnorm' which has larger blooms with very double petalage.

The objective of the hybridization of this rose variety for garden use was to create a new and distinct variety with unique qualities, such as:

1. Uniform and abundant flowers;
2. Vigorous growth;
3. Fragrant flowers;
4. Disease resistance.

This combination of qualities is not present in previously available commercial cultivars of this type and distinguishes 'POULnorm' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULnorm' was selected in spring, 1986 by the inventors as a single plant from the progeny of the aforementioned hybridization.

Asexual reproduction of 'POULnorm' by traditional budding was first done by L. Pernille and Mogens N. Olesen in August 1986. This initial and other subsequent propagations conducted in controlled environments have demonstrated that the characteristics of 'POULnorm' are true to type and are transmitted from one generation to the next.

BRIEF DESCRIPTION OF THE DRAWING

The accompanying color illustration shows, as true as is reasonably possible to obtain in color photographs of this type, the typical characteristics of the buds, flowers, leaves, and stems of 'POULnorm'. Specifically illustrated in SHEET 1:

1. Stem showing branching and the attachment of leaves, buds, and peduncles;
2. Flower bud, partially opened bud, and open bloom;
3. Flower petals, detached;

Specifically illustrated in SHEET 2:

4. Sepals, receptacle, and pedicel;
5. Flowering stem as well as a bare stem exhibiting thorns;
6. Leaves.

DETAILED DESCRIPTION OF THE VARIETY

The following is a description of 'POULnorm', as observed in its outdoor growth in a field nursery in Jackson County, Oreg. Observations were conducted duuring September, 1998 on plants aged eighteen months. Color references are made using The Royal Horticultural Society (London, England) Colour Chart, 1995, except where common terms of color are used.

For a comparison, several physical characteristics of the rose variety 'POULisab', a hybrid tea rose variety from the same inventors described and illustrated in U.S. Plant patent application Ser. No. 09/270,177 filed Mar. 15, 1999 are compared to 'POULnorm' in Chart 1.

CHART 1

| | 'POULnorm' | 'POULisab' |
|---|---|---|
| Color of bloom after opening. | Red Group 53A. | Red Group 46A. |
| Basal petal spot, after opening. | White Group 155C. | Yellow Group 4A–4C. |
| Petalage. | Very double, 45–50 petals. | Very double, 55–70 petals. |

Parents:
*Seed parent.*—Unnamed seedling.
*Pollen parent.*—'Norita'.
Classification:
*Botanical.*—*Rosa hybrida.*
*Commercial.*—Climber.

FLOWER AND FLOWER BUD

Blooming habit: Recurrent.
Flower bud:
*Size.*—Upon opening, 20 mm–30 mm in length from base of receptacle to end of bud.
*Bud form.*—Pointed ovoid.
*Bud color.*—As sepals unfold, Greyed-Purple Group 183A–184A. Greyed-Purple Group 183B with intonations of Red Group 53A at ¼ opening.
*Sepals.*—Upper and lower sides Green Group 143C. Intonations on upper and lower side of sepals of Greyed-Red Group 180A. Weak to moderate foliaceous appendages on three of the five sepals. Exterior surfaces of sepals slightly pubescent. Interior of sepals pubescent. Stipitate glands are present in limited quantities on the margins of sepals. Sepals are 20 to 25 mm long and 10 to 15 mm wide. Apex shape is subulate.
*Receptacle.*—Surface: Smooth. Shape: Funnel to urn-shaped. Size: Medium to large, 8 mm(l)×10–12 mm (w). Color: Yellow-Green Group 146C.
*Peduncle.*—Surface: Smooth, with limited numbers of stipitate glands present. Length: 50–60 mm average length. Color: Yellow-Green Group 144B with intonations of Greyed-Red Group 181A. Strength: Strong.
*Borne.*—Generally with 1–3 buds per flowering stem.
Flower bloom:
*Fragrance.*—Moderate to strong spicy, floral scent.
*Duration.*—As a cut flower 3 to 5 days. The blooms have a duration on the plant of approximately 5 to 8 days. Petals fall cleanly away from plant.
*Size.*—Average flower diameter is 100 mm when fully open.
*Form.*—Shape of flower when viewed from the side: Upon opening, upper part: Flattened convex. Upon opening, lower part: Convex. Open flower, upper part: Flat. Open flower, lower part: Concave to flat.
*Petalage.*—Very double. Average range: 45–50 petals under normal conditions with 4–8 petaloids.
Color:
*Upon opening, petals.*—Petals: Upper petals surface with velvety texture. Inner Petals: Upper Surface: Red Group 53A. Reverse Side: Red Group 53A. Outer Petals: Upper Surface: Red Group 53A. Reverse Side: Red Group 53A.
*Upon opening, basal petal sports.*—Outer Side: Yellow Group 3B. Inner Side: Yellow Group 3A.
*After opening, petals.*—Inner Petals: Upper Surface: Red Group 34A. Reverse Side: Red Group 34A. Outer Petals: Upper Surface: Red Group 34A. Reverse Side: Red Group 34A.
*After opening, basal petal spots.*—Outer Side: White Group 155C. Inner Side: White Group 155C.
General tonality: On open flower is an intense dark red, Red Group 34A. No change in the general tonality at the end of the 5th day. Afterwards, general tonality is Red Group 34B to 34C.
Petals:
*Petal reflex.*—Innermost petals reflexed slightly. Outermost petals more reflexed, with a few petals double reflexed.
*Petal edge.*—Entire.
*Shape.*—Obovate, with cuspidate apex.
*Petaloids.*—4–8 petaloids. Petaloids are 7 to 12 mm long and 4 to 6 mm wide. Petaloids are velvety in texture. Color is Red Group 34A.
*Texture.*—Thick and velvety.
*Arrangement.*—Imbricated.
Reproductive organs:
*Pistils.*—Quantity: 18 to 20. Length: 4 to 6 mm.
*Pollen.*—Color: Yellow Group 13B. Quantity: Average.
*Anthers.*—Color: Immature: Yellow Group 12C. Mature: Greyed-Orange Group 163C and Brown Group 200B. Quantity: 20 to 25.
*Filaments.*—Color: Green-Yellow Group 1B. When flower is opening there is a strong intonations of Greyed-Purple Group 185B. Length: 5–8 mm. Quantity: 20 to 25.
*Stigmas.*—Generally at same position as anthers. Color: Yellow-Green Group 145D.
*Styles.*—Color: Green-White Group 157A. There is a strong intonation of Greyed-Purple Group 185B on upper half of style length.
*Hips.*—None observed.

PLANT

Plant growth: Vigorous and upright climber. When grown as a budded field grown plant on *Rosa multiflora* understock, the average height of the plant itself is 220–300 cm. The width is approximately 100 cm.
Stems:
*Color.*—Young wood: Yellow-Green Group 146C. Older wood: Yellow-Green Group 146C.
*Thorns.*—Incidence: Light number of thorns. Size: Average length: 6 mm. Color: Yellow-Green Group 147D. Shape: Concave with downward curve.
*Surface.*—Young wood: Smooth. Older wood: Smooth.
Plant foliage: Normal number of leaflets on leaves in middle of the stem: 5 leaflets.
*Leaf size.*—Small. 100–110 mm (l)×85–95 mm (w).
*Quantity.*—Average.
*Color.*—Upper Leaf Surface: Green Group 137A. Lower Leaf Surface: Green Group 138B. Juvenile foliage: Green Group 146B.
*Anthocyanin.*—Location: Upper and lower leaflets surfaces, rachis, petioles, stipules, stems, peduncles, and thorns. Color: Greyed-Red Group 178A.
Plant leaves and leaflets:
*Stipules.*—Size: 14 mm–18 mm. Color: Green Group 144B. Texture: Smooth.

*Petiole.*—Length: 25 mm–30 mm. Color: Green Group 144B. Texture: Smooth upper surface wth some fine hairs. Margins: With limited numbers of stipitate glands.

*Rachis.*—Color: Green Group 144B. Underneath: Smooth upper surface; some rachis with fine hairs. Margins: With limited numbers of stipitate glands.

*Leaflet.*—Edge: Serrated. Shape: Ovate. The leaflet's apex is acuminate. The leaflet's base is rounded. Arrangement: The leaflets are arranged in an odd-pinnate formation. Venation: The leaflets are veined in a reticulate pattern. Texture: Leaves are thick: Upper side of leaflet is moderately glossy. Lower side of leaflet is matte.

Disease resistance: Average resistance to mildew, black spot, and Botrytis under normal growing conditions in Jackson County, Oreg.

Winter hardiness: 'POULnorm' has been found to be resistant to damage from cold in USDA Zone 8 and USDA Zone 7.

We claim:

1. A new and distinct variety of rose plant of the climbing rose class, substantially as herein illustrated and described as a distinct and novel rose variety due to its abundant, dark-red fragrant flowers, vigorous growth, disease resistance, and extended period of bloom.

* * * * *

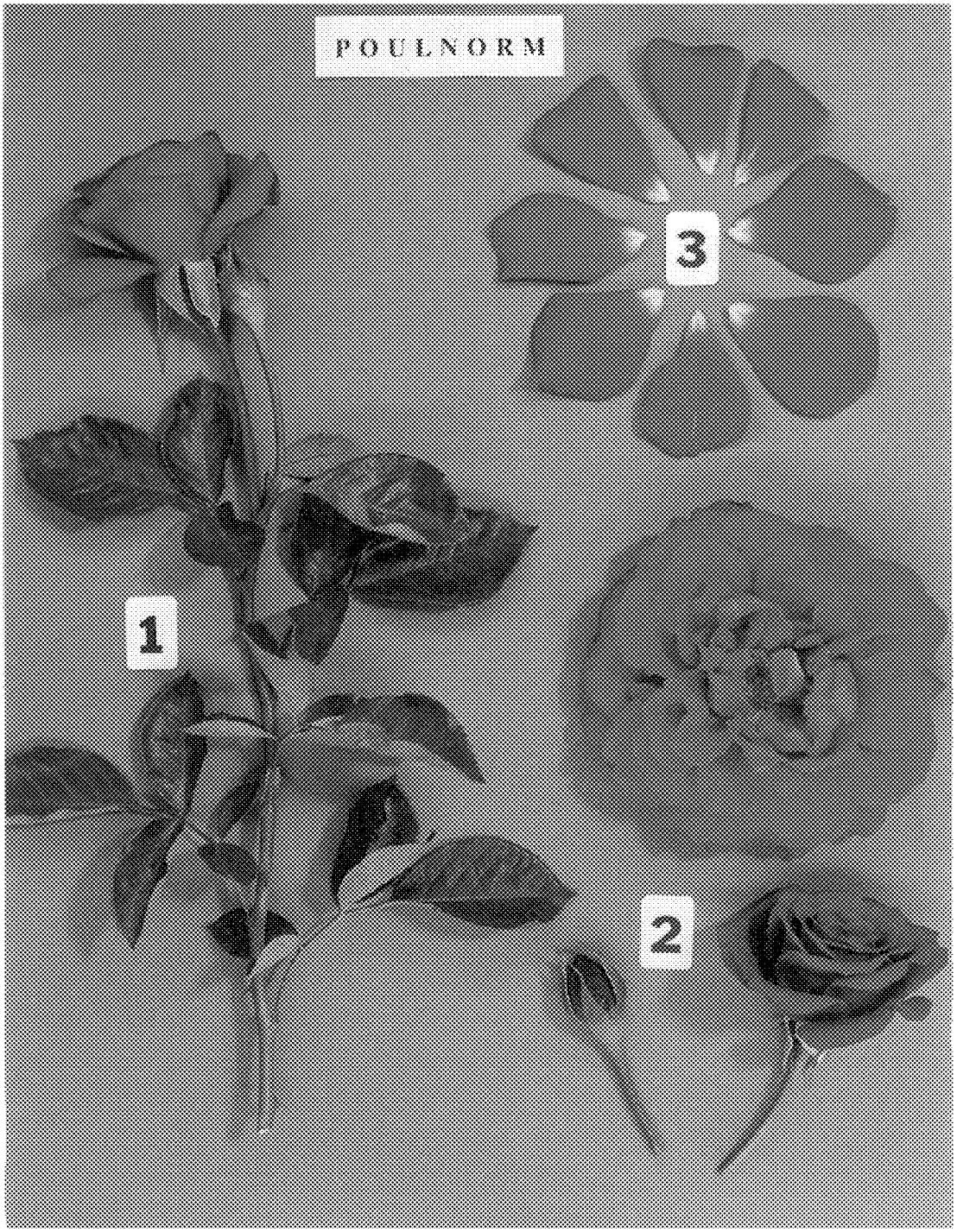
POULNORM
1
2
3

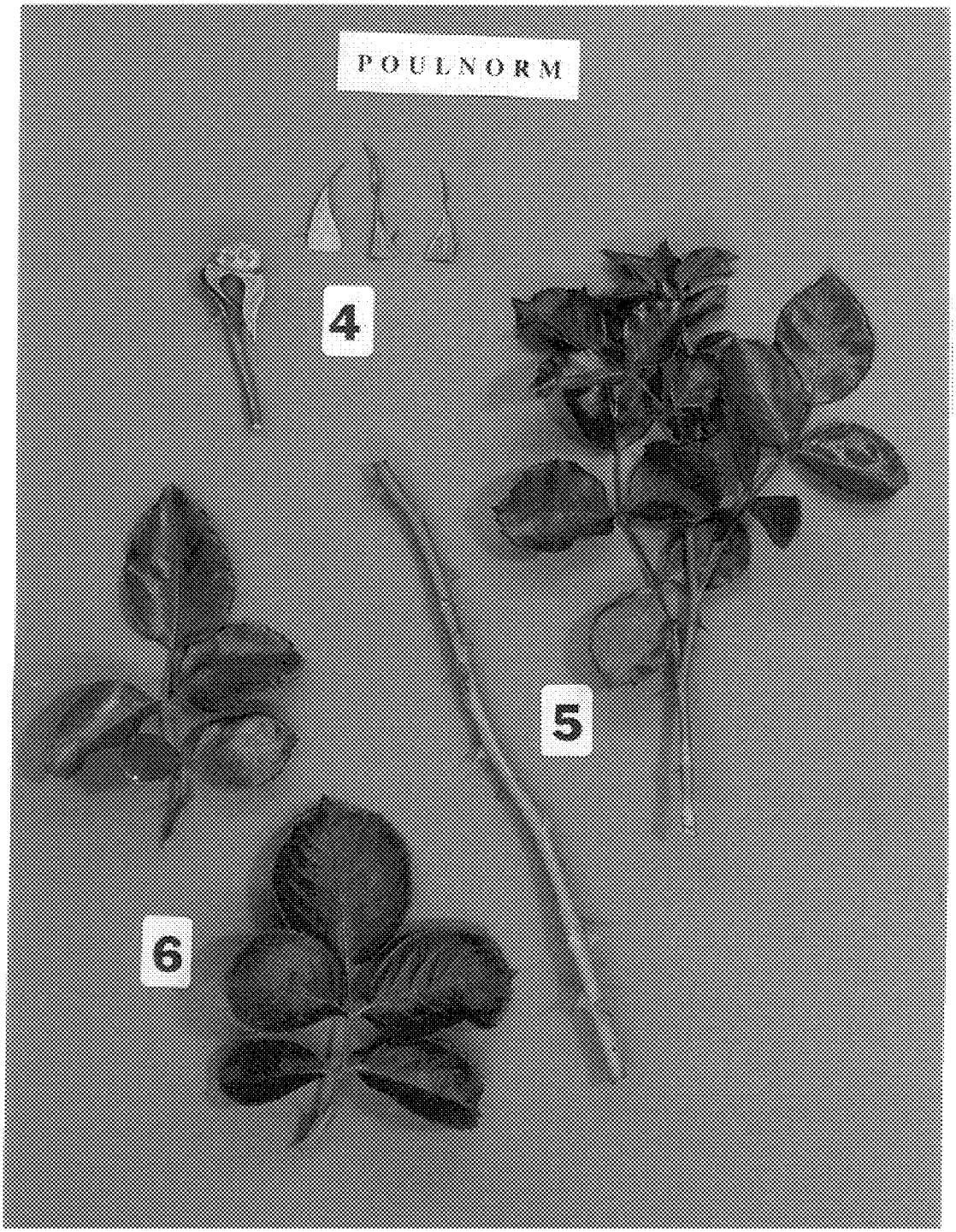
POULNORM
4
5
6